United States Patent [19]

Hymes

[11] 4,125,110

[45] Nov. 14, 1978

[54] MONITORING AND STIMULATION ELECTRODE

[76] Inventor: Alan C. Hymes, 3828 Wilmatt Hill Rd., Hopkins, Minn. 55343

[21] Appl. No.: 849,405

[22] Filed: Nov. 7, 1977

Related U.S. Application Data

[63] Continuation of Ser. No. 785,225, Apr. 6, 1977, abandoned, which is a continuation of Ser. No. 635,008, Nov. 25, 1975, abandoned.

[51] Int. Cl.² ................................................ A61B 5/04
[52] U.S. Cl. ............................ 128/2.06 E; 128/2.1 E; 128/418; 128/DIG. 4; 106/79; 260/760
[58] Field of Search ............... 128/2.06 E, 2.1 R, 404, 128/410, 411, 416–418, DIG. 4; 106/79; 260/760

[56] References Cited

U.S. PATENT DOCUMENTS

| 1,631,265 | 6/1927 | Harris | 260/760 |
|---|---|---|---|
| 1,777,162 | 9/1930 | Biddle | 106/79 |
| 2,555,037 | 5/1951 | Jensen | 128/417 |
| 2,943,627 | 7/1960 | Howell | 128/416 |
| 3,027,333 | 3/1962 | Friedman | 128/417 A |
| 3,547,105 | 12/1970 | Paine | 128/2.06 E |
| 3,607,788 | 9/1971 | Adolph | 128/418 X |
| 3,665,064 | 5/1972 | Mosier et al. | 128/417 X |
| 3,720,209 | 3/1973 | Bolduc | 128/2.06 E |
| 3,911,906 | 10/1975 | Reinhold, Jr. | 128/2.06 E |
| 3,989,050 | 11/1976 | Buchatter | 128/417 X |
| 3,993,049 | 11/1976 | Kater | 128/2.06 E |
| 3,998,215 | 12/1976 | Anderson et al. | 128/2.06 E |
| 4,002,221 | 1/1977 | Bucholter | 128/2.06 E X |
| 4,016,869 | 4/1977 | Reichenberger | 128/2.1 E |

FOREIGN PATENT DOCUMENTS 675,494 12/1963 Canada .................................. 128/417

OTHER PUBLICATIONS

Nasa Tech. Brief, by Mosier, TSP69-10598, Nov. 1969.

*Primary Examiner*—Lee S. Cohen
*Attorney, Agent, or Firm*—Norman P. Friederichs

[57] ABSTRACT

An improved combination electrode for use in monitoring and stimulation medical applications is provided having an electrical current conductor including a connector plug and a skin-interfacing substrate material, this substrate being a composition such as mixture of a natural organic polysaccharide and hydric alcohol having electrically conductive and adhesive properties.

21 Claims, 4 Drawing Figures

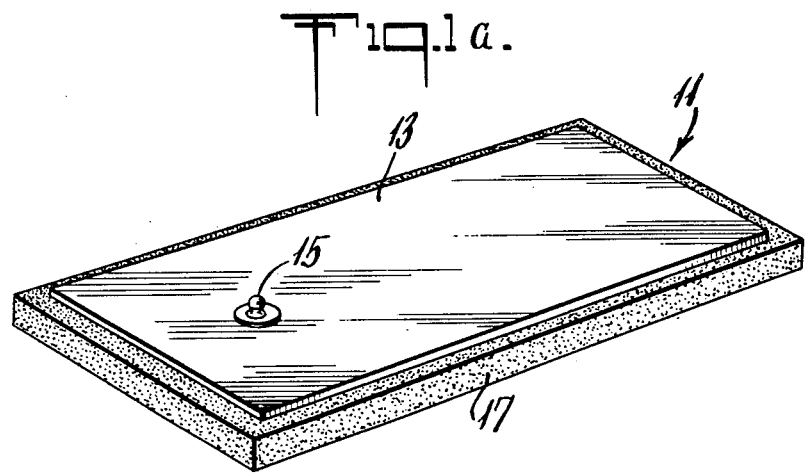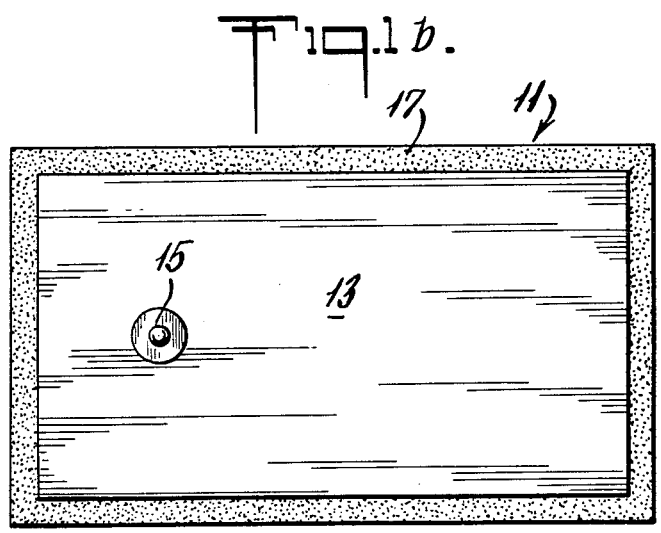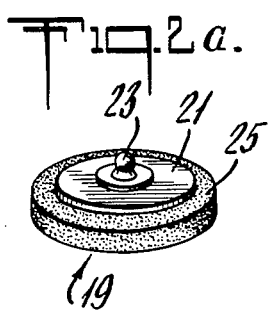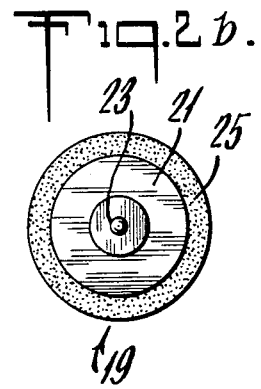

MONITORING AND STIMULATION ELECTRODE

The present application is a continuation of U.S. patent application Ser. No. 785,225 filed Apr. 6, 1977 entitled "Monitoring and Stimulation Electrode" (now abandoned) which was a continuation of U.S. Patent application Ser. No. 635,008 filed Nov. 25, 1975 entitled "Monitoring and Stimulation Electrode" (now abandoned).

BACKGROUND OF THE INVENTION

Medical electrodes have in the past taken many shapes and forms. Principally, they have been shaped according to the use for which they are intended. Electrodes used in monitoring apparatus, such as EKG and EEG machines, commonly have small round contact surfaces. While electrodes used in such stimulation apparatus as pain control tend to be larger and have most often rectangularly or other conveniently shaped contact surfaces. Whether intended for monitoring or stimulation use, a design objective for each electrode group has been, and continues to be, good electrical signal transmission between a patient's skin surface and the electrical wiring connected to a particular piece of apparatus. Not only is efficient signal transmission across the epidurumconductor interface desirable, but so is effective signal transmission which is free of current concentration points or "hot spots."

Prior art electrodes offer combination structures including a metallic or otherwise conductive support member to which an electrical wire from an associated apparatus may be attached. Some electrodes teach the incorporation of an electrode paste or gel applied directly to the conductive support member to enhance conductivity across the skin-electrode interface.

Other electrodes teach the additional incorporation of an open cellular skin interface pad secured to a conductive support member. This pad as shown in U.S. Pat. No. 3,817,252, is very often a sponge material and functions to hold or contain an electrolyte solution. The electrolyte solution enhances conductivity across the skin-pad interface. Alternately, this interface pad can be saturated with electrode pastes or gels which will not turn or evaporate as readily as electrolyte solutions.

None of these prior art electrodes offer a structure which will maintain constant, efficient and effective electrical transmission for long periods of time without the need for additional electrode paste, gel or solution. Moreover, with these electrodes there is a tendency for the electrolyte film to separate and/or to flow to a non-uniform thickness. Under these conditions, sections of the conductive support member could be exposed to the skin. Local hot spots will result which can cause discomfort to the patient if not causing burns to the patient's skin.

These prior art electrodes must be secured to the surface of a patient's skin with medical tape or other securing mediums. Very often an electrode secured in this manner will pull away from skin creating a partial or total interruption in signal transmission.

More recent improvements in the electrode art include composite electrodes using electroconductive tape as the skin interfacing medium. This tape has a film of pressure sensitive adhesive for engaging the skin surface. In these electrodes, the adhesive has been doped with a quantity of electrically conductive particles such as carbon powder as disclosed in U.S. Pat. No. 3,911,906 in order to provide an electrical path to the skin. This doping can create non-uniform electrical transmission through the adhesive. Moreover, in the presence of large quantitites of skin moisture, these adhesives lose their ability to adhere to the skin surface, thus pulling away and drastically changing the electrical characteristics of the electrode.

An objective of this invention, therefore, is to provide a composite electrode with a skin-interface substrate which will perform a similar function to, and therefore eliminate the need for an electrolyte solution, electrode paste or electrode gel.

Another objective of this invention is to provide this electrode with a skin-interface substrate having adhesive properties which will enable the electrode to adhere to the skin without the use of tape or other securing means and which will not lose adhesiveness in the presence of large quantitites of skin moisture.

Another objective is to provide this electrode wherein the adhesive skin-interface substrate is electrically conductive this conductivity being uniform throughout the substrate.

A further objective is to provide this electrode with a skin-interface substrate which will maintain a uniform thickness and will not separate to expose sections of a conductive support member to the skin.

An even further objective is to provide such an electrode including such a skin-interface substrate where this substrate will not break down under long periods of use.

SUMMARY OF THE INVENTION

The objectives of this invention are accomplished in a medical electrode which may include a conductive support and electrical current distribution member. Preferably, this member may be a sheet or layer of metallic or other conductive material having mounted thereon or secured thereto a fastener or other suitable object for securing positive electrical contact between said conductive support member and cables connecting to external electrical equipment. Abutting one side of said support member, and in electrical contact therewith, may be an electrically conductive skin-interface substrate. This substrate may be principally a colloidal dispersion of a naturally-occurring, organic, hydrophilic polysaccharide such as karaya and other compounds. Included amongst these compounds may be sodium-based salts and glycerol.

DESCRIPTION OF THE DRAWINGS

The novel features of this invention as well as the invention itself, both as to its organization and method of operation, will best be understood from the following description taken in connection with the accompanying drawings in which like characters refer to like parts, and in which:

FIG. 1a shows a perspective view of a stimulation electrode;

FIG. 1b shows an elevation view of the electrode of FIG. 1a;

FIG. 2a shows a perspective view of a monitoring electrode;

FIG. 2b shows an elevation view of an electrode of FIG. 2a.

DETAILED DESCRIPTION OF THE INVENTION

Medical electrodes are intended for usage as efficient and effective signal transmission mediums between a patient's skin and an electro-medical apparatus. Primary to their operation is a uniform conductivity through the electrode itself and a uniform conductivity across the electrode-skin interface. Uniform conductivity through an electrode is most often interrupted by a non-uniformity in electrode material, while uniform conductivity across the electrode-skin interface is most often interrupted by a separation of some or all of the electrode interfacing material in contact with a patient's skin.

The electrode at hand is intended to have adhesive properties for maintaining contact with the skin as well as possessing a certain amount of elasticity for movement with the skin in addition to a uniform configuration for contact with the skin and the passage of uniform current densities to the skin. This electrode is intended to be easily handled and to have a long, realistic operating life while being non-irritating to the patient.

A stimulation electrode configuration 11 is shown in FIGS. 1a and 1b. Included in this configuration 11 is a conductive support and electrical current distibution member 13 which is cut, stamped or otherwise shaped out of a piece of metallic foil. The shape to which this conductive support member 13 is formed will depend upon the particular application in which it is used. Most commonly, as shown in the FIGS. 1a and 1b, this member 13 is rectangular in shape. The conductive support member 13 shown herein is of aluminum foil 6 mils thick. This foil thickness provides a pliable conductive support member 13 which can easily be pressed to conform to the skin surface of a patient while maintaining sufficient strength to perform the support function. Alternatively, this conductive support and current distribution member 13 may be made of wire mesh, conductive cloth or conductive polymer material. When an alternate material is used for this member 13, an appropriate strength and thickness is to be chosen to yield a pliable yet sufficiently strong member 13.

Secured to the outer surface of the support and distribution member 13 is an electrically conductive swaged snap fastener 15. This fastener 15 is utilized as the electrical connector coupling by which electrical wires may be attached to said distribution member 13. The fastener 15 is riveted or otherwise mechanically and electrically attached to said support and distribution member extending perpendicularly from the outer surface of said support and distribution member 13.

Abutting the inner surface of said support and distribution member 13 is an electrically conductive skininterface substrate 17. This substrate 17 is a layer of material which will be described below.

The substrate 17 is a rectangular sheet of material of uniform thickness of from 1/16 to ¼ inch which is cut to shape so as to extend beyond each edge of the support and distribution member 13 a distance of about ⅛ inch when the support and distribution member 13 has been centered upon the substrate 17. This will assure that no part of the support member 13 will contact the skin. As will be discussed below, this substrate 17 has adhesive properties, thus, when brought into contact with the support and distribution member 13, intimate contact is maintained with that member 13.

In operation, the electrode 11 is applied with the substrate 17 in direct contact with the skin. The adhesive properties of the substrate 17 eliminate the need for tape or other securing measures to hold the electrode 11 in continuous contact with the skin. As described above, the fastener 15 receives electrical signals from an external apparatus. These signals are conducted into the support member 13 which in turn directly conducts them into the uniform substrate 17. In this manner, current densities are uniformly distributed over the area of the substrate 17 in contact with the support and distribution member 13 and in turn, uniformly transmitted to the skin surface in contact with the substrate 17.

A monitoring electrode configuration 19 is shown in FIGS. 2a and 2b. In this configuration 19 as in the stimulation electrode configuration 11, a sheet of aluminum foil or equivalent material forms a conductive support member 21. The size, shape and thickness of this support member 21 may be varied; most commonly, it may be round, of about 1–1½ inches in diameter and about 1–10 mils thick.

A swaged snap fastener 23 is riveted to the center of aluminum foil support member 21. Abutting the side of the support member 21 opposite the fastener 23 is a uniform sheet of conductive substrate 25. This substrate 25 is centered on the support member 21 being about 1/16 to ¼ inch thick and of a size to extend about ⅛ inch beyond the edge of the support member 21. The substrate 25 can have identical physical, chemical and electrical properties as the substrate 17 used in the stimulation electrode 11.

In operation, electrical signals present in a patient's body are transmitted across the skin-substrate interface and into the substrate 25 where they are conducted to the support member 21, the fastener 23 and its associated wiring to the monitoring apparatus; respectively.

Primary to the unique structure of the electrodes 11, 19 for eliminating signal artifact, a disruption of the signal profile, is the ability of the substrate 17, 25 to adhere to the skin surface when there is motion between the electrode and the skin. The hydrophilic adhesive properties of the electrode enhance the interface transmission of signals. Motion of the electrode does not produce a feedback artifact as there occurs with the use of pastes and gels. The structure and composition of the substrate 17, 25 material enables it to possess physical, chemical and electrical properties which reduce or eliminate feedback artifact under motion by the electrode.

The substrate 17, 25 is a colloidal dispersion of a natural organic hydrophilic polysaccharide and salts in an alcohol as the continuous phase.

In its principal embodiment, the substrate 17, 25 is a sheet of karaya gum composition as sold commercially by Hollister, Inc., of Chicago, Ill. A patent assigned to Hollister covering this composition is U.S. Pat. No. 3,640,741. The composition is available in prepared sheet form and alternately, as a powder which must be mixed and cured. The composition contains karaya, glycerin, propylene glycol and other additives in the following proportions:

|  | Nominal Amounts of Ingredients | Range of Ingredients |
|---|---|---|
| Karaya | 40 gm | 30 to 60 gm |
| Glycerin | 57 gm | 30 to 90 gm |
| Propylene Glycol | 3 cc | 1 to 10 gm |
| Sodium Chloride | .07 gm | .01 to 1.5 gm |
| Water | 3 cc | 1 to 10 gm |
| Calcium Chloride | .06 cm | .01 to 1.5 gm |

This table shows that the hydrophilic polysaccharide (karaya) may be present in an amount of 21% to 65% and alternatively between 36% and 65% by weight. The hydric alcohol (glycerin) may be present in an amount of between 33% and 74% or between 33% and 52% by weight. The water may be present in an amount of at least about 0.6%, for example, 0.6% to 6.0% by weight. The electrolytic salt (sodium chloride) is shown to be at least about 0.006%, preferably, at least 0.016% (i.e., 0.006% to 0.9%). Propylene glycol is shown between 0.6% and 6.0%. The calcium chloride is shown to be present in an amount of 0.006% to 0.9% by weight.

The product is poured into sheets and heated under pressure to 175° F for a length of time to form sheets of the substrate material.

The karaya composition is hydrophilic. When one of the substrates 17, 25, comprising this composition is applied to the skin, body moisture as well as body salts and heat are absorbed by this composition increasing its tackiness and causing the surface of the material to soften and to tend to go into solution. As a result, the substrate will flow into pores and other irregularities in the skin, creating a mechanical-interlock bond with the skin in addition to the already present adhesive bond. The bonding and elastic properties of the electrode are enhanced as it "ages" in contact with the skin.

The flow condition eliminates air spaces between the skin and the substrate-composition to greatly reduce the impedance across the interface which in turn greatly reduces the electrically generated heat normally created at this interface. While the surface portion of the substrate-composition will flow, the greater portion of its mass will remain intact.

Thus, the material resists separation or the development of irregular thicknesses. As a result, two heat and/or burn producing conditions, i.e., a high resistance across the interface due to an air layer creating high temperatures over the entire interface, and a physical contact of the conductive support member 13, 21 directly with the skin creating a shunt of current to a small area thus generating extreme temperatures in that area, are avoided. The electrical transmission properties of the karaya gum electrode are enhanced as it "ages" in contact with the skin.

A secondary electrical effect is also improved as the electrode "ages." Present during the operation of all electrodes is a battery effect created at the skin interface due to the capacitance across this interface. This battery effect causes some current to circle backward toward its source of flow to create eddy currents. This causes a "tingling sensation" in the skin. With this electrode, as water and body salts are absorbed into the electrode substrate, the interface area becomes more ionically, i.e., electrically, homogeneous thus reducing the battery effect and the resulting "tingling sensation" causing eddy currents.

The above described karaya composition offers an electrode substrate with favorable properties having a limited life. After continuous use for 2 or 3 days, this karaya composition will break down or dissolve and run or separate much like the electrode pastes and gels it was intended to be an improvement over. The working life of this karaya composition can be extended by reducing body heat at the electrode.

An alternate embodiment offers an alternate karaya formulation which offers improved physical properties as well as a longer working life. Similar electrical characteristics are maintained with this alternate karaya formulation.

The alternate karaya formulation includes karaya powder in a glycerin suspension as well as particles of silicone rubber in the suspension. This alternate formulation provides an alternate composition containing a glycerin solution, powdered natural karaya gum within the working range of ingredients described above as well as the additional additive, Silastic*, according to the following proportions by weight: glycerin solution-82 grams; karaya powder-100 grams; Silastic*,-7 grams. Silastic* is a commercially available silicone rubber from Dow Corning. The glycerin solution contains sodium chloride, propylene glycol and glycerol according to the following proportions: sodium chloride-9 grams; propylene glycol-18 cc; glycerol-1000 cc.

*Trademark of Dow Corning

To prepare this alternate compound, the solution and powders are mixed at room temperature and/or heated to 75° C to cause the mixture to solidify into a pliable or plastic mass. This plastic mass is then rolled into sheets of desired size and thickness and allowed to cool or alternately poured into molds and then placed under pressure and heat until excess moisture is driven off and then cooled. The amount of heat applied to the mixture will depend upon the batch size being cured. Care should be taken to obtain a product mass which resists flow. This can be done by maintaining heat for longer periods of time.

The silicone rubber additive reduces the flow characteristics and increases the tensile strength of the colloidal dispersion as well as increasing its melting point or resistance to flow under heat, as compared to the original karaya compound without silicone rubber.

The alternate karaya compound embodiment may be directly used in place of the original karaya compound. It has similar electrical impedance properties as well as a number of similar chemical and physical properties. More specifically, an electrode combination comprising a sheet of this alternate karaya compound as the skin-interface substrate will adhere to the skin, and ply as the skin moves similarly to the original karaya compound. It has less impedance to electrical signals but has slightly less affinity for the moisture and salts from the skin. As moisture is absorbed, however, it will dissolve and flow into skin irregularities. This alternate compound will not dissolve as readily in the presence of water nor will it flow or break down as readily with the application of heat as the original karaya compound. Thus, this silicone enhanced compound has held up from one to two days longer than the original karaya formulation under similar operating conditions.

Other materials may be added to form an alternate karaya compound in place of the silicone rubber. These other substitute compounds will also enhance the mechanical properties of the original substrate compound by cross-linking karaya molecules, but to varying degrees. These cross-linking materials must form homogenous dispersion and have free radicals to react with karaya molecules. As an example, such materials may include gelatin, corn starch, cellulose, polyvinyl chloride, polyvinyl acetate, urethane, epoxy resins, certain polyesters and calcium salts.

Karaya gum being a natural organic polysaccharide will support microbe growth. It is important to add an antimicrobial to each compound to inhibit bacteria growth. Equally important, the substrate compound should be nonreactive with the patient's skin. Efforts should be directed to maintain a proper pH and to add only hypo-allergenic compounds to the mixture. The compound can be subjected to a heavy dosage of gamma radiation.

Additional variations may also be made in the electrode. An open cell sponge or similar material may be impregnated with the karaya compound. This sponge could be used to act as a support structure for shaping the karaya compound sheet for a particular use.

For other applications, the electrical fastener 15 and the method of making an electrical connection to the electrode could be changed. Instead of the fastener 15, a wire could be attached to the support member 13 in a "pig-tail" arrangement for mating an electrical cable away from the electrode structure itself. This pig-tail connection to the electrode would permit connecting the electrode without the possibility of disturbing its position on the skin.

Since many changes and many embodiments could be made to the above-described invention without departing from the scope thereof, it is intended that all matter contained in the above description be interpreted as illustrative and not in the imiting sense.

What is claimed:

1. An electrode for establishing electrical connection to a patient's skin, comprising:
    an electrically conductive backing and current distribution member;
    electrical terminal means attached to said member, said terminal means being adapted for connection of the electrode to an electrical wire; and
    a substrate attached to said backing and current distribution member for interfacing with the patient's skin, said substrate comprising a homogeneous material including between 21% and 65% high molecular weight hydrophilic polysaccharide material, at least about 0.006% electrolytic salt, at least about 0.6% water and an alcohol, said substrate being sufficiently pliant to permit conformation of the shape of the electrode to the body contours, said substrate being sufficiently firm to prevent penetration of the body contours through the substrate thereby preventing contact of the backing member with the skin, and said substrate being uniformly conductive thereby providing a homogeneous conducting surface to the skin.

2. An electrode according to claim 1 wherein said substrate material includes a high molecular weight naturally occurring polysaccharide gum.

3. An electrode according to claim 2 wherein said polysaccharide gum comprises karaya.

4. An electrode according to claim 3 wherein said substrate material includes sufficient karaya gum to provide adhesiveness and firmness.

5. An electrode according to claim 2 wherein said substrate material includes sufficient hydric alcohol to provide plasticity to said substrate.

6. An electrode according to claim 1 wherein said substrate extends beyond the edges of said backing and current distribution member to further prevent direct contact between said member and the patient's skin.

7. An electrode according to claim 6 wherein said substrate extends beyond the edges of said member for a distance of approximately ⅛ inch.

8. An electrode according to claim 1 wherein said substrate comprises from 21% to 65% karaya gum, from 74% to 33% glycerin, 0.6% to 6.0% propylene glycol, from 0.006 to 0.9% sodium chlloride, from 0.6% to 6.0% water and from 0.006% to 0.9% calcium chloride by weight.

9. The electrode of claim 1 wherein said substrate comprises karaya powder, silicone rubber particles and glycerin, said karaya powder and silicone particles being suspended in said glycerin.

10. The electrode of claim 1 wherein said electrically conductive backing and current distribution member is a member selected from the group consisting of wire mesh, conductive cloth and conductive polymer material.

11. An electrode for establishing electrical connection to a patient's skin, comprising:
    a conductive backing and current distribution member;
    electrical terminal means attached to said member for permitting electrical connection to the electrode; and
    a skin interfacing substrate attached to said backing and current distribution member, said substrate comprising a homogeneous sheet of material having electrical conduction, adhesive, elastic and plastic properties for adhering to the patient's skin and establishing uniform electrical conduction throughout the contact area with the skin, said material including a humectant, an electrolyte, hydric alcohol, and a natural polysaccharide gum, said hydric alcohol being present in an amount of from 33% to 52% and said natural polysaccharide gum being present in an amount of from 65% to 36% by weight.

12. An electrode according to claim 11 wherein said sheet includes a sufficient proportion of said natural polysaccharide gum to provide adhesive and elastic properties, and a sufficient proportion of alcohol to provide said plasticity.

13. An electrode according to claim 12 wherein said natural polysaccharide gum comprises karaya gum.

14. An electrode according to claim 13 wherein said sheet further includes a binder compund having free radicals for establishing cross-linking with the karaya.

15. The electrode of claim 14 wherein said binder compound is a member selected from the group consisting of gelatin, corn starch, cellulose, polyvinyl chloride, polyvinyl acetate, urethane, epoxy resins, polyesters and calcium salts.

16. An electrode for establishing electrical connection to an patient's skin, comprising:
    a conductive backing and current distribution member;
    electrical terminal means attached to said member for permitting electrical connection to the electrode; and
    a substrate attached to said backing and current distribution member for interfacing with the patient's skin, said substrate comprising a sheet of material comprising approximately between 36% and 65% natural polysaccharide gum,
    approximately between 52% and 33% hydric alcohol,
    and at least 0.016% electrolytic salt.

17. An electrode according to claim 16 wherein said natural polysaccharide gum has a large molecular weight and has hydrophilic characteristics for making a conductive colloidal suspension in said hydric alcohol.

18. An electrode according to claim 16 wherein said natural polysaccharide gum comprises karaya gum.

19. An electrode for establishing electrical connection to a patient's skin, comprising:
    a conductive backing and current distribution member;

electrical terminal means attached to said member for permitting electrical connection to the electrode; and a substrate attached to said backing and current distribution member for interfacing with the patient's skin, said substrate comprising a sheet of material including approximately between 30 and 60 parts by weight natural polysaccharide gum, approximately 30 to 90 parts by weight hydric alcohol, and at least about 0.01 parts by weight electrolytic salt.

20. The electrode of claim 19 wherein said substrate comprising a sheet of material including by weight between about 30 to 60 parts karaya gum, about 30 to 90 parts glycerin, about 0.01 to 1.5 parts sodium chloride and about 1 to 10 parts water.

21. The electrode of claim 20 wherein said substrate comprises about 40 parts karaya gum, about 57 parts glycerin, about 3 parts propylene glycol, about 0.07 parts sodium chloride, about 3 parts water and about 0.06 parts calcium chloride by weight.

* * * * *

UNITED STATES PATENT AND TRADEMARK OFFICE
CERTIFICATE OF CORRECTION

PATENT NO. : 4,125,110

DATED : November 14, 1978

INVENTOR(S) : Dr. Alan C. Hymes

It is certified that error appears in the above-identified patent and that said Letters Patent are hereby corrected as shown below:

column 1
Line 23, change "patient'skin" to --patient's skin--.
Line 44, change "turn" to --run--.

IN THE CLAIMS:

Claim 8, line 4, change "chlloride" to --chloride--.

Signed and Sealed this

Thirteenth Day of March 1979

[SEAL]

Attest:

RUTH C. MASON
Attesting Officer

DONALD W. BANNER
Commissioner of Patents and Trademarks